United States Patent [19]

Pickering et al.

[11] 4,194,509
[45] Mar. 25, 1980

[54] PRECONNECTED CATHETER DRAINAGE SYSTEM

[75] Inventors: Keldon S. Pickering, Basking Ridge; Keith T. Ferguson, Scotch Plains, both of N.J.

[73] Assignee: C. R. Bard, Inc., Murray Hill, N.J.

[21] Appl. No.: 895,459

[22] Filed: Apr. 11, 1978

[51] Int. Cl.² ............................................. A61M 27/00
[52] U.S. Cl. .................................. 128/350 R; 128/247
[58] Field of Search ............... 128/348, 349 R, 349 B, 128/349 BV, 350 R, 350 V, 351, 247, DIG. 9, DIG. 16, DIG. 18, 294–295

[56] References Cited

U.S. PATENT DOCUMENTS

| | | |
|---|---|---|
| 3,022,543 | 2/1962 | Baird, Jr. et al. . |
| 3,139,468 | 6/1964 | Wheat . |
| 3,276,929 | 10/1966 | Ferch . |
| 3,315,986 | 4/1967 | Quick . |
| 3,484,121 | 12/1969 | Quinton . |
| 3,513,429 | 5/1970 | Helsop . |
| 3,526,683 | 9/1970 | Heslop et al. . |
| 3,669,095 | 6/1972 | Kobavashi et al. . |
| 3,768,476 | 10/1973 | Raitto ............................. 128/349 R |
| 3,825,001 | 7/1974 | Bennet et al. ................... 128/349 R |
| 3,890,962 | 6/1975 | Ramsey . |
| 3,959,052 | 5/1976 | Stanek . |
| 3,985,950 | 10/1976 | Maltz . |
| 3,990,661 | 11/1976 | De Groef . |
| 4,004,705 | 1/1977 | Fujio . |
| 4,009,793 | 3/1977 | Minesinger et al. . |
| 4,079,738 | 3/1978 | Dunn et al. ................... 128/DIG. 16 |

*Primary Examiner*—Robert W. Michell
*Assistant Examiner*—C. F. Rosenbaum
*Attorney, Agent, or Firm*—Dennison, Dennison, Meserole & Pollack

[57] ABSTRACT

A preconnection system wherein the catheter is sealed to the drainage tube adaptor by a "tamper-evident" shrink band or wrap during the manufacture and assembly of the components and prior to sterilization. The shrink band incorporates a tear strip with a gripping tab, both of which overlie the adaptor in a recess formed at the juncture between the adaptor and catheter funnel.

8 Claims, 6 Drawing Figures

PRECONNECTED CATHETER DRAINAGE SYSTEM

BACKGROUND OF THE INVENTION

Over 600,000 nosocomial (hospital-acquired) urinary tract infections are developed per year. This constitutes approximately 40% of all infections developed in hospitals, with such infections normally requiring treatment involving hospitalization for several days at costs which have been averaging $1,000 per incidence.

One of the primary causes of urinary tract infections is the entry of bacteria into the established drainage system at the point of connection between the Foley catheter and the tubing connector or drainage tube adaptor.

This point of joining between the catheter and the tubing connector has been found to be particularly troublesome in that disconnection, either accidentally or intentionally without authorization, frequently occurs. This not only greatly increases the possibility of bacteria entering into the established drainage system, but also could have a serious effect on any flow metering or measuring which might be involved. For example, in the management of some patients, it is very essential that the urine output be accurately measured. Thus, a urine meter will normally be interposed between the catheter and collection bag. Any tampering with the catheter connection to the drainage system would affect the readings obtained and could in turn have an adverse effect on patient management.

While systems have heretofore been used which have been referred to as "preconnected" systems, such merely involved preconnecting the catheter to the drainage bag or drainage tube adaptor by conventional telescopic frictional engagement at the point of assembly or manufacture. No provision was made for preventing disconnection, preventing tampering with the connection, or providing evidence of either tampering or disconnection.

SUMMARY OF THE INVENTION

The invention herein basically proposes a positive "tamper-evident" seal for affecting a positive interlock between the catheter and the drainage tube adaptor in a manner whereby any possibility of accidental disconnection at this point is precluded and any intentional disconnection is immediately evident.

In providing for such a sealing of the catheter to the drainage tube adaptor, all of the above noted problems with regard to contamination, improper measurements, and the like, which might arise from a disconnection at this important juncture, are avoided. The seal itself is provided about the telescopically engaged adaptor and catheter at the time of the assembly of the drainage system kit and, normally, prior to sterilization whereby the entire kit can be simultaneously sterilized. The catheter thus remains an integral part of the drainage system up to and during the period of use in connection with a patient. As indicated, during use in particular, accidental opening of the system between the adaptor and the catheter is positively prevented, and an intentional opening of the system at this point is readily detectable. By the same token, provision is made for an intentional disengagement of the drainage system from the patient-carried catheter in those circumstances wherein such a disengagement is essential for any of a variety of legitimate purposes, such as replacement of the drainage bag, irrigation, or the like. While a reengagement of the drainage system is possible, such as when connecting a new drainage bag, the nature of the seal of the invention is such so as to always present a visual indication of a break in the original sealed system, notwithstanding a subsequent reengagement of the system.

Basically, during the initial assembly or manufacture of the system, the tapered tip of the tubing connector is frictionally engaged within the catheter funnel with the exposed end of the funnel providing a shoulder or stepped portion at the juncture with the connector. A wrap of heat shrinkable material is then wrapped about the juncture, overlapping both the connector and the catheter funnel, and subsequently heat shrunk into tight sealing engagement with the connector and funnel. The material will preferably be of a highly visible color, such as red, whereby removal will be readily apparent.

Removal of the seal, in those cases wherein a replacement of the drainage bag is required, or under similar legitimate circumstances, is effected by means of a tear strip incorporated into the wrap, or more specifically laminated thereto and oriented so as to be positioned immediately outward of the end of the funnel to lie within the step portion of the juncture. This positioning of the tear strip within the stepped portion of the juncture is of particular significance in that a reversely folded tab is provided and can be retained in the recess formed by the step in a manner so as to avoid irritation of the patient's skin, this funnel-connector junction frequently being in direct contact with the patient's thigh. Further, the tear strip so positioned enables an opening of the seal directly at the mouth of the catheter funnel whereby, in addition to providing a clear indication of a breaking of the seal, also provides a clear funnel for the attachment of a replacement drainage system or other equipment as desired.

DESCRIPTION OF THE PREFERRED EMBODIMENT

Figure 1:
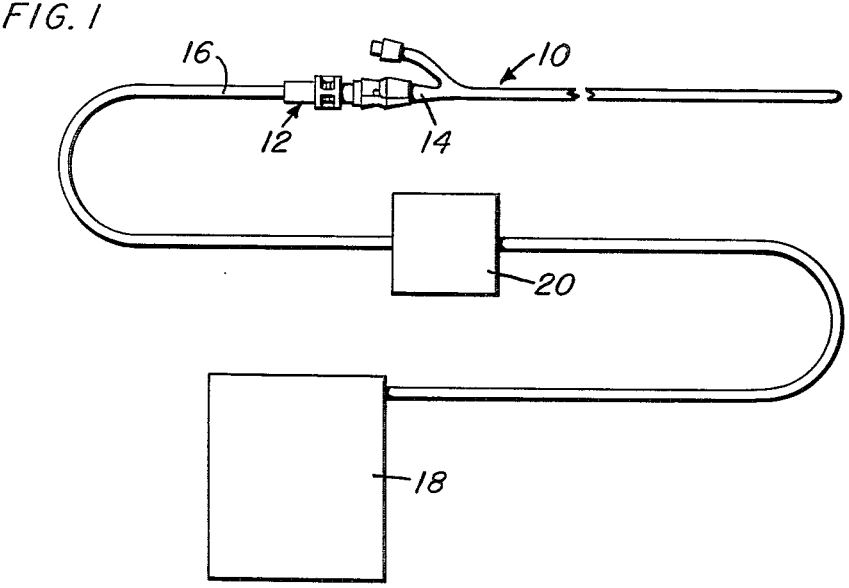
FIG. 1 schematically illustrates a drainage system incorporating the preconnected and sealed Foley catheter.

Referring now more specifically to the drawings, attention is directed initially to FIG. 1 wherein a drainage system has been generally and schematically illustrated. This system will normally include a Foley catheter 10 having a drainage tube adaptor or tubing connector 12 telescopically engaged within the catheter funnel 14 at the proximal end of the catheter. The tubing connector is in turn bonded to the leading end of the drainage tube 16 which ultimately leads to the drainage or collection bag or container 18. If so desired, appropriate apparatus, such as for example a urine meter 20, can be interposed between the tubing connector 12 and the drainage bag 18.

Figure 2:
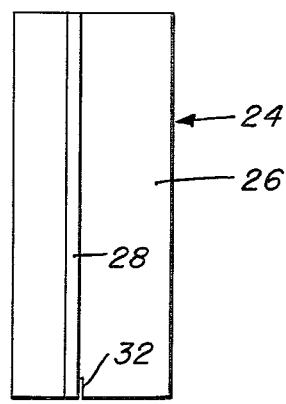
FIG. 2 is an exploded perspective view of the drainage tube adaptor, the catheter funnel and the shrink wrap.
Figure 2:
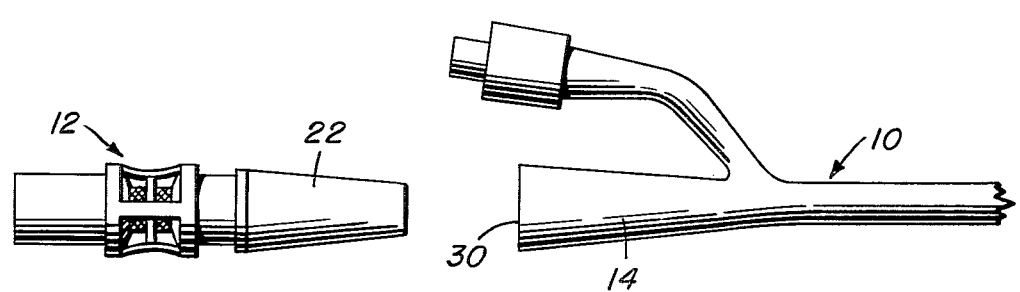

In the conventional system as described above, the tubing connector 12 is merely frictionally engaged within the catheter funnel 14, even in systems wherein a preconnection is effected so as to provide a kit incorporating all of the components. With such a frictional engagement, and in the absence of any means preventing a ready disengagement, all of the above detailed problems of bacteria introduction, improper meter readings, and the like are encountered. The present invention proposes providing an effective "tamper-evident" interlock at this connection. In regard thereto, attention is particularly directed to the specific components involved, such components being individually illustrated in FIG. 2.

The catheter funnel 14, as suggested by its name, is a taper or funnel shaped configuration integrally defined on the proximal end of the catheter 10. This funnel 14 receives the elongated tapered leading end or tip 22 of the tubing connector or drainage tube adaptor 12. The opposite end of the connector 12 is conventionally bonded to the drainage tube 16.

Figure 3:
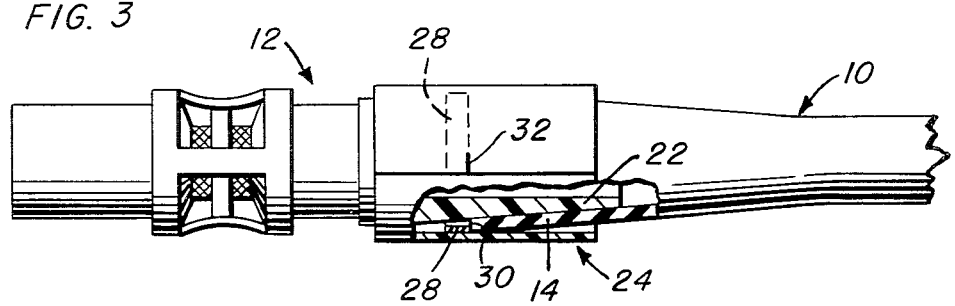
FIG. 3 is an assembled view of the components of FIG. 2, with a portion broken away for purposes of illustration and prior to a shrink sealing of the wrap.
Figure 4:
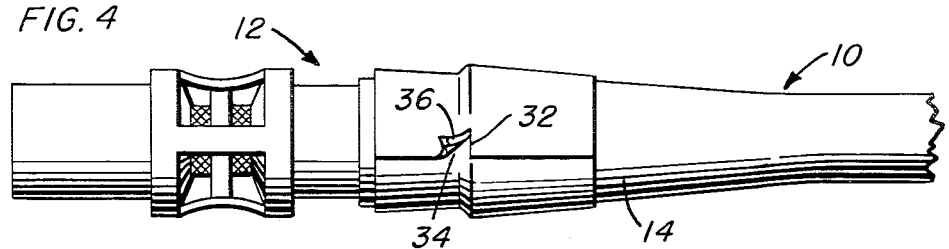
FIG. 4 is a view similar to FIG. 3 with the wrap shrunk into position and with the pull tab formed.

These assembled components, with attention also being directed to FIG. 3, are enclosed within a wrapping or wrap 24 of heat shrink material. This wrap 24 will be of a length so as to completely encircle the telescopically engaged connector tip 22 and funnel 14 with the ends of the wrap 24 sufficiently overlapped so as to insure a complete encircling of the juncture and avoid any gaps. The width of the wrap 24 is to be such so as to provide an overlapping and positive engagement of a significant portion of both the connector tip 22 and the funnel 14 sufficient so as to avoid any accidental longitudinal disengagement of the tip from the funnel.

The heat shrinkable wrap 24 consists of a length of heat shrinkable adhesive tape 26 and a thin tear strip 28 of heat shrinkable film laminated to the adhesive face of the tape 26 along the length thereof. Both the tape 26 and the strip 28 are to be made of an appropriate heat shrinkable resin such as, for example, polyolefins and more particularly polyethylene, but not limited thereto. A slit 32 is provided to assist in the preferred removal.

As will be appreciated from the drawings, the extreme open end 30 of the catheter funnel 14, when receiving the connector tip 22 therein, forms in effect a shoulder projecting outwardly from the tip 22 at the juncture therewith and completely thereabout. This in turn forms a recess or stepped portion at this juncture. The shrink wrap 24, with the adhesive face inward, is wrapped about the connection or juncture between the connector 12 and the catheter funnel 14 in a manner whereby the tear strip 28 is positioned about the tip 22 immediately outward of the shoulder forming end of the funnel 14. It will of course be appreciated that a sufficient area of the adhesive face of the adhesive tape 26 is provided beyond the tear strip 28 so as to firmly attach to the connector tip 22 both adhesively and through the subsequently described shrink action. This arrangement of the wrap about the connected adaptor and catheter funnel will possibly be best appreciated from FIG. 3. With continued reference to this Figure, it will also be noted that the slight slit 32 is extended inward from the leading edge of the applied wrap 24 parallel to and immediately adjacent that edge of the tear strip 28 facing the end 30 of the funnel 14. While a single slit in this position is preferred, slits can be provided along both edges of the tear strip 28.

After a winding or wrapping of the wrap or tape about the telescopically joined adaptor tip 22 and catheter funnel 14, the wrap 24 is subjected to sufficient heat so as to effect the desired shrinkage and subsequent bonding to the joined components, this bonding being, for all practical purposes, permanent in nature, in that any removal thereof would require a destruction of the wrap in a readily visible manner.

Immediately subsequent to the shrinkage of the wrap 24, and normally while the material of the wrap is still heated and pliable, the leading end of the tear strip 28, adjacent the slit 32, is folded back on itself so as to generally define a V notch 34 and a flattened gripping tab 36. This tab 36 facilitates a gripping of the leading end of the tear strip 28, which is now shrunk into the stepped or recessed portion of the juncture and normally relatively difficult to engage. The actual use of the tear strip, as mentioned previously, is so as to enable an intentional disconnection of the catheter from the remainder of the drainage system for specific purposes such as irrigation, replacement of the drainage bag, and the like.

Figure 5:
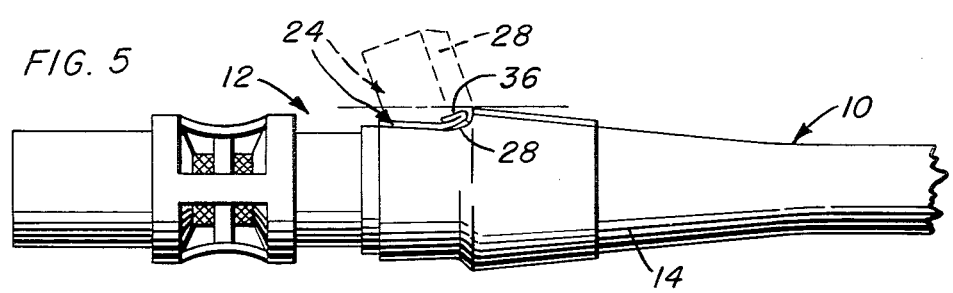
FIG. 5 is a rotated view of the sealed juncture illustrating the recessed nature of the tab.
Figure 6:
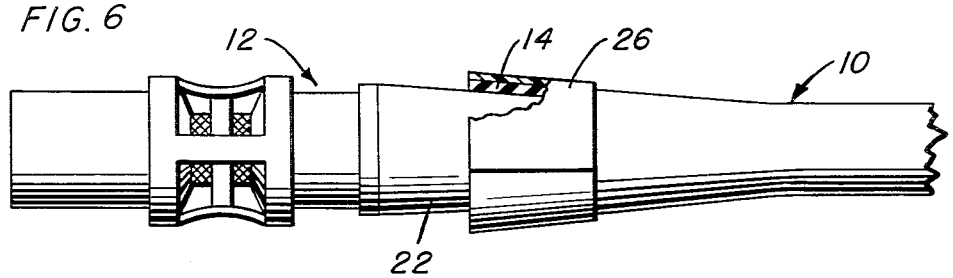
FIG. 6 is a view similar to FIG. 4 with the seal broken and the adaptor portion of the wrap stripped away.

Because of the positioning of the tear strip immediately at the end 30 of the catheter funnel 14, it will be appreciated that upon an opening of the wrap by a pulling of the tear strip, which of course extends the full length of the wrap, the wrap will be divided into a first section which peels entirely off and is removed from the connector tip 22, and the second section which remains engaged with the catheter funnel 14 whereby the desired disengagement of the telescopic interconnection can be affected. The actual tearing of the wrap will follow the slit 32 and the corresponding edge of the strip 28 which lies immediately adjacent the funnel end 30. This is suggested in phantom lines in FIG. 5. Once the wrap section has been severed and removed by a pulling of the tear strip, as seen in FIG. 6, the breaking of the seal will be readily apparent. This of course is highly desirable even when a breaking of the seal is authorized and part of a set procedure in that one is always aware of the broken seal and can follow appropriate procedures so as to maintain the integrity of the system within the limits of the procedures required. By the same token, the broken seal will provide a clear visible warning in those instances wherein the breaking or opening of the seal was not authorized.

At this point attention is directed again to FIG. 5 wherein the flattened tab 36 has been illustrated in elevation. It will be noted that the tab, positioned within the stepped or recessed portion of the juncture, is itself recessed below the outer surface of the wrapped catheter funnel. This is considered of particular significance in that the folded back tab 36 is generally roughened and could cause irritation were it to contact and rub against the patient's body. In this regard, and in the use of Foley catheters as proposed herein, there is frequent direct contact between the funnel and connector interlock and the patient's thigh.

From the foregoing, it should be appreciated that a unique preconnection arrangement has been devised for a Foley catheter drainage system whereby one of the major areas of bacteria contamination has been substantially eliminated. This has been effected by providing a positive "tamper-evident" seal about the juncture between the telescopically interconnected catheter funnel and drainage tube adaptor. This seal, in the nature of a heat shrunk wrap, is applied during the initial manufacture or assembly of the drainage system kit and, while providing what might be considered a permanent seal of the catheter to the system, also provides for a disconnection of the catheter from the remainder of the system by a severing of the seal. This severing of the seal is effected in a manner whereby full access to the catheter, normally retained in the patient, is available for additional procedures, such as irrigation or the connection of replacement drainage equipment.

The foregoing is considered illustrative of the principles of the invention. As modifications and changes may occur to those skilled in the art, it is not desired to limit the invention to the exact construction and operation shown and described. Accordingly, all suitable modifications and equivalents may be resorted to, falling within the scope of the invention as claimed.

We claim:

1. For use in a preconnected assembly for drainage and the like, a catheter, a drainage tube adaptor, said catheter having a proximal end, said adaptor being preconnected to said proximal end of said catheter, said drainage tube adaptor including a projecting end portion telescopically and frictionally received within the catheter through the proximal end of the catheter, a juncture defined between the proximal end of the catheter and the adaptor end portion, and means for maintaining the connection of said drainage tube adaptor to said catheter, said means comprises a heat shrinkable material encircling the juncture and extending about both the end portion of the adaptor and the proximal end of the catheter to each side of the juncture to both effect a sealing thereof and provide a visual indication of a disconnection effort.

2. The assembly of claim 1 wherein said heat shrinkable material includes a tear strip positioned so as to encircle the adaptor end portion immediately outward of the proximal end of the catheter.

3. The assembly of claim 2 including a tab defined on the leading end of the tear strip, a recess defined about the preconnected adaptor and catheter proximal end immediately adjacent said juncture, said tab being positionable within said recess.

4. The assembly of claim 3 wherein said tab is defined by a slit in the wrap along the side of the tear strip adjacent said juncture and a rearwardly folded leading section of the tear strip adjacent said slit.

5. For use in a preconnected assembly for drainage and the like, a catheter, a drainage tube adaptor, said catheter having a proximal end, said adaptor being preconnected to said proximal end of said catheter, and means for maintaining the connection of said drainage tube adaptor to said catheter and for providing an indication of a disconnection effort, said means comprising a heat shrinkable material overlying and encircling the preconnected adaptor and proximal end of said catheter.

6. The assembly of claim 5 wherein the heat shrinkable material includes a tear strip positioned so as to encircle the adaptor immediately outward of the proximal end of the catheter, a tab defined on the leading end of the tear strip, and a recess defined about the preconnected adaptor and catheter proximal end, said tab being positionable within said recess.

7. An assembly comprising a Foley catheter, a drainage tube adaptor and a "tamper-evident" seal, said Foley catheter incorporating a connection funnel, said adaptor including a projecting tip telescopically received within the catheter funnel, the open end of the catheter funnel defining a juncture with the telescopically received tip, said seal comprising a heat shrunk wrap about said juncture and the catheter funnel and adaptor tip to the opposite side thereof.

8. The assembly of claim 7 wherein the juncture defines a recess circumferentially about the connection, said wrap incorporating a tear strip with a tab on the leading end thereof, said tear strip and tab being positioned within the juncture defined recess immediately adjacent the end of the catheter funnel.

* * * * *

REEXAMINATION CERTIFICATE (1312th)
United States Patent [19]
Pickering et al.

[11] B1 4,194,509
[45] Certificate Issued Jun. 26, 1990

[54] PRECONNECTED CATHETER DRAINAGE SYSTEM

[75] Inventors: Keldon S. Pickering, Basking Ridge; Keith T. Ferguson, Scotch Plains, both of N.J.

[73] Assignee: C. R. Bard, Inc., Murray Hill, N.J.

Reexamination Reqs:st:
No. 90/001,721, Feb. 24, 1989
No. 90/001,761, Apr. 24, 1989

Reexamination Certificate for:
Patent No.: 4,194,509
Issued: Mar. 25, 1980
Appl. No.: 895,459
Filed: Apr. 11, 1978

[51] Int. Cl.$^5$ ............................................. A61M 27/00
[52] U.S. Cl. ..................................... 604/111; 604/283
[58] Field of Search ................. 604/111, 283, 905; 128/DIG. 18

[56] References Cited

U.S. PATENT DOCUMENTS

| | | |
|---|---|---|
| 3,332,418 | 5/1964 | Brody . |
| 3,485,239 | 12/1969 | Vanderbeck . |
| 3,583,460 | 6/1971 | Faust et al. . |
| 3,677,243 | 7/1972 | Nerz . |
| 3,677,244 | 7/1972 | Hassinger . |
| 3,768,476 | 10/1973 | Raitto . |
| 3,814,137 | 6/1974 | Martinez . |
| 3,873,018 | 3/1975 | Donnay . |
| 3,952,869 | 4/1976 | Sansom . |
| 4,079,738 | 3/1978 | Dunn et al. . |

FOREIGN PATENT DOCUMENTS

50-23551  8/1975  Japan .

OTHER PUBLICATIONS

Blakiston's New Gould Medical Dictionary, 1956 by the McGraw-Hill Book Company, Inc., pp. 217, 463.
"Infection and the Catheter", by Frank Hinman Jr., M.D., Urology, 1972, pp. 7-8.
"Prevention of Catheter-Induced Post-Prostatectomy Infection. Effects of Systemic Cephaloridine and Local Irrigation with Neomycin-Polymyxin Through Closed-Drainage Catheter System", by George W. Drach, et al., The Journal of Urology, vol. 105, Jun. 1971, pp. 840-842.
"Detection, Prevention and Management of Urinary Tract Infections", by Calvin M. Kunin, M.D., 2nd Edition, 1974, pp. 147-148.

*Primary Examiner*—C. Fred Rosenbaum

[57] ABSTRACT

A preconnection system wherein the catheter is sealed to the drainage tube adaptor by a "tamper-evident" shrink band or wrap during the manufacture and assembly of the components and prior to sterilization. The shrink band incorporates a tear strip with a gripping tab, both of which overlie the adaptor in a recess formed at the juncture between the adaptor and catheter funnel.

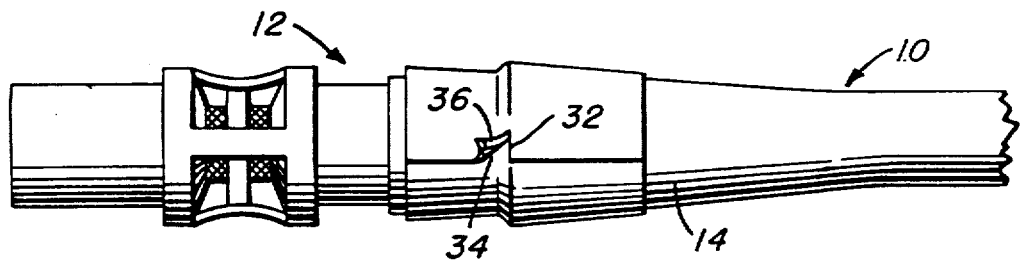

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *